US011331032B2

(12) United States Patent
Scharf

(10) Patent No.: US 11,331,032 B2
(45) Date of Patent: May 17, 2022

(54) ELECTROCARDIOGRAM METHOD FOR LACTATE THRESHOLD DETECTION

(71) Applicant: John Edward Scharf, Sacramento, CA (US)

(72) Inventor: John Edward Scharf, Sacramento, CA (US)

(*) Notice: Subject to any disclaimer, the term of this patent is extended or adjusted under 35 U.S.C. 154(b) by 278 days.

(21) Appl. No.: 16/510,912

(22) Filed: Jul. 13, 2019

(65) Prior Publication Data

US 2021/0007619 A1    Jan. 14, 2021

(51) Int. Cl.
*A61B 5/00* (2006.01)
*A61B 5/352* (2021.01)
*A61B 5/024* (2006.01)
*A61B 5/282* (2021.01)
*A61B 5/316* (2021.01)
*A61B 5/332* (2021.01)
*A61B 5/339* (2021.01)

(52) U.S. Cl.
CPC ............ *A61B 5/352* (2021.01); *A61B 5/0006* (2013.01); *A61B 5/02405* (2013.01); *A61B 5/282* (2021.01); *A61B 5/316* (2021.01); *A61B 5/332* (2021.01); *A61B 5/339* (2021.01); *A61B 5/486* (2013.01); *A61B 5/6823* (2013.01); *A61B 5/6831* (2013.01); *A61B 5/7257* (2013.01)

(58) Field of Classification Search
CPC ..... A61B 5/0456; A61B 5/0404; A61B 5/044; A61B 5/6823; A61B 5/0006; A61B 5/486; A61B 5/7257; A61B 5/04085; A61B 5/6831; A61B 5/02405; A61B 5/04012
See application file for complete search history.

(56) References Cited

U.S. PATENT DOCUMENTS

2016/0007864 A1* 1/2016 Scharf ................ A61B 5/02438
600/301

* cited by examiner

*Primary Examiner* — Rex R Holmes
(74) *Attorney, Agent, or Firm* — Ingenium Patents LLC; Peter R. Kramer

(57) ABSTRACT

Lactate threshold device (LTD) assists subjects in improving athletic performance and maximizing calorie burn. LTD digitizes the electrocardiogram (ECG) obtained from a chest belt with a first signal analyzer, and telemeters the ECG to a second signal analyzer. LTD uses a novel algorithm to convert the telemetered ECG from the time to frequency domain, utilizing a digital signal processing method called fast fourier transform based spectral analysis. LTD determines whether lactate threshold (LT) has been reached, and furthermore calculates heart rate, heart rate variability, and heart rate and power zones. LTD displays the determined variables on a local or remote display. Subject using LTD obtains feedback during a real-time exercise regimen in the field that has aerobic (below LT) and anaerobic (above LT) zones. By utilizing an exercise program with aerobic and anaerobic zones, both sprint and endurance fitness levels are improved, and weight loss potential is maximized.

3 Claims, 12 Drawing Sheets
(6 of 12 Drawing Sheet(s) Filed in Color)

FFT-based Spectral Analysis Software Algorithm and Digital
Signal Processing by Microprocessor with Floating Point Unit FFT-based Spectral Analysis Software Algorithm and Digital Signal Processing by Microprocessor with Floating Point Unit Heartbeat Monitoring Device Android Phone Remote Display Algorithm to Observer (coach, trainer, fan, self) during Heavy Exercise Smartphone Display or Watch Display Cardiac, Respiratory, and THM lines, after FFT processing Heartbeat Measuring Device

ELECTROCARDIOGRAM METHOD FOR LACTATE THRESHOLD DETECTION

TECHNICAL FIELD

This disclosure relates generally to wearable exercise devices. More specifically, the disclosure provides an electrocardiogram system and digital signal processing method for detecting lactate threshold to improve athletic performance and increase calorie burn in real-time in the field.

SUMMARY

Systems and methods described herein include the design and use of a wearable exercise device for lactate threshold detection. In some cases, the lactate threshold device (LTD) can be or act as a multi-faceted tool to assist subjects in improving athletic performance and dramatically increasing calorie burn. Users adjusting their athletic endeavor in real-time through usage of the LTD often exercise more efficiently, and significantly increase calorie burn, thereby improving their weight loss endeavor as well. In its more detailed application, LTD is a smart device with two signal analyzers that may determine, integrate, compare, evaluate, and display electrocardiogram, heart rate, heart rate variability, lactate threshold data, and heart rate exercise zones as well as cycling/running power zones. Without being limited thereto, the athletic endeavor or exercise with which the device can be used and the methods utilized, can include, for example, running, swimming, cycling, high intensity interval training, cross country skiing, speed skating, and other endurance events and sports. The device can be used for football, soccer, basketball, rock climbing, hiking, trekking, and backpacking, for example, as well as training and coaching in other sports. The device can additionally be used in high intensity sports where heart rate, heart rate variability, and electrocardiogram interpretation may be important for athlete safety and/or performance in real-time in the field.

Systems and methods described herein provide a portable, low-power, wireless, real-time device, with two signal analyzers. As described herein, embodiments may analyze the electrocardiogram, using Fast Fourier Transform (FFT) based spectral analysis, for lactate threshold detection in the field, under heavy exercise conditions, in real-time, including training and competition conditions, and telemeter the digital signal processing results to the exercising athlete on a local display, and/or to their trainers, coaches, or any observer with a remote display.

One embodiment of an LTD system includes a heart rate chest belt transmitter, with two electrocardiogram electrodes, and a first signal analyzer that serves as a signal gatherer, conditioner, and digitizer. The first signal analyzer wirelessly transmits the conditioned electrocardiogram and instantaneous heart rate signals to the second signal analyzer. The second signal analyzer may determine parameters such as electrocardiogram interpretation, instantaneous and average heart rate, heart rate variability, lactate threshold, and heart rate exercise zones as well as cycling/running power zones. The second signal analyzer generally has one or more processors electrically coupled to the telemetry receiving unit, which receives the telemetered data from the first signal analyzer. Further, the second signal analyzer may include a storage device having stored computer-executable instructions which, when executed by the one or more processors, implements a digital signal processing method.

The digital signal processing method that is novel in this invention includes transforming the digitized electrocardiogram parameters from a time domain into a frequency domain, and subsequently determining whether lactate threshold has been reached. The second signal analyzer may use a Fast Fourier Transform (FFT) based spectral analysis to transform the electrocardiogram from the time domain to the frequency domain, and analyze the result for the occurrence of fundamental cardiac and harmonic cardiac spectral lines, as well as their satellite components caused by heart rate variability. Further, feedback may be calculated and shown to an observer by the local or remote display, including a lactate threshold evaluation, and subsequently heart rate exercise zones and cycling/running power exercise zones (in Watts). These calculated exercise zones, based upon lactate threshold, may be prescribed in real-time during the exercise event. In some embodiments, the lactate threshold evaluation may provide instructions to guide a subject in obtaining and maintaining maximal lactate steady state (MLSS) or functional threshold power (FTP), typically for twenty to sixty minutes, of heavy exercise.

In some embodiments, the time spent in the aerobic training zone may be monitored, and after a designated time spent training in the aerobic training zone, instructions for a user to increase training activity to enter into the anaerobic training zone may be shown on the local and/or remote display. LTD is able to define aerobic and anaerobic exercise zones precisely and accurately, as the occurrence of lactate threshold is the key defining parameter in defining aerobic from anaerobic training zones. The designated time in each heart rate zone (in beats per minute) or in each cycling/running power zone (in Watts) may be adjustable by the exercising subject or trainer. For example, the designated time spent in the anaerobic training zone and the designated time spent in the aerobic training zone may be altered by a user or trainer, once LTD has detected and calculated lactate threshold in real-time. In another example, the designated time spent in the anaerobic training zone and the designated time spent in the aerobic training zone are configured to automatically adjust according to a preselected and/or custom prescribed training program.

It should be understood that in the above described devices, apparatuses, systems and methods, and those elsewhere herein, that one or more of the features can be specifically excluded, and one or more other features described in connection with other devices, apparatuses, systems and methods, can be specifically added to or additional included. For example, one embodiment describes two signal analyzers, with a telemeter transmitting the conditioned and digitized electrocardiogram from the first signal analyzer to the second signal analyzer. To those skilled in the art, in another embodiment, the first and second signal analyzers may be combined into a unified signal analyzer.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Illustrative embodiments will hereafter be described with reference to the accompanying drawings.

DETAILED DESCRIPTION

Figure 1:
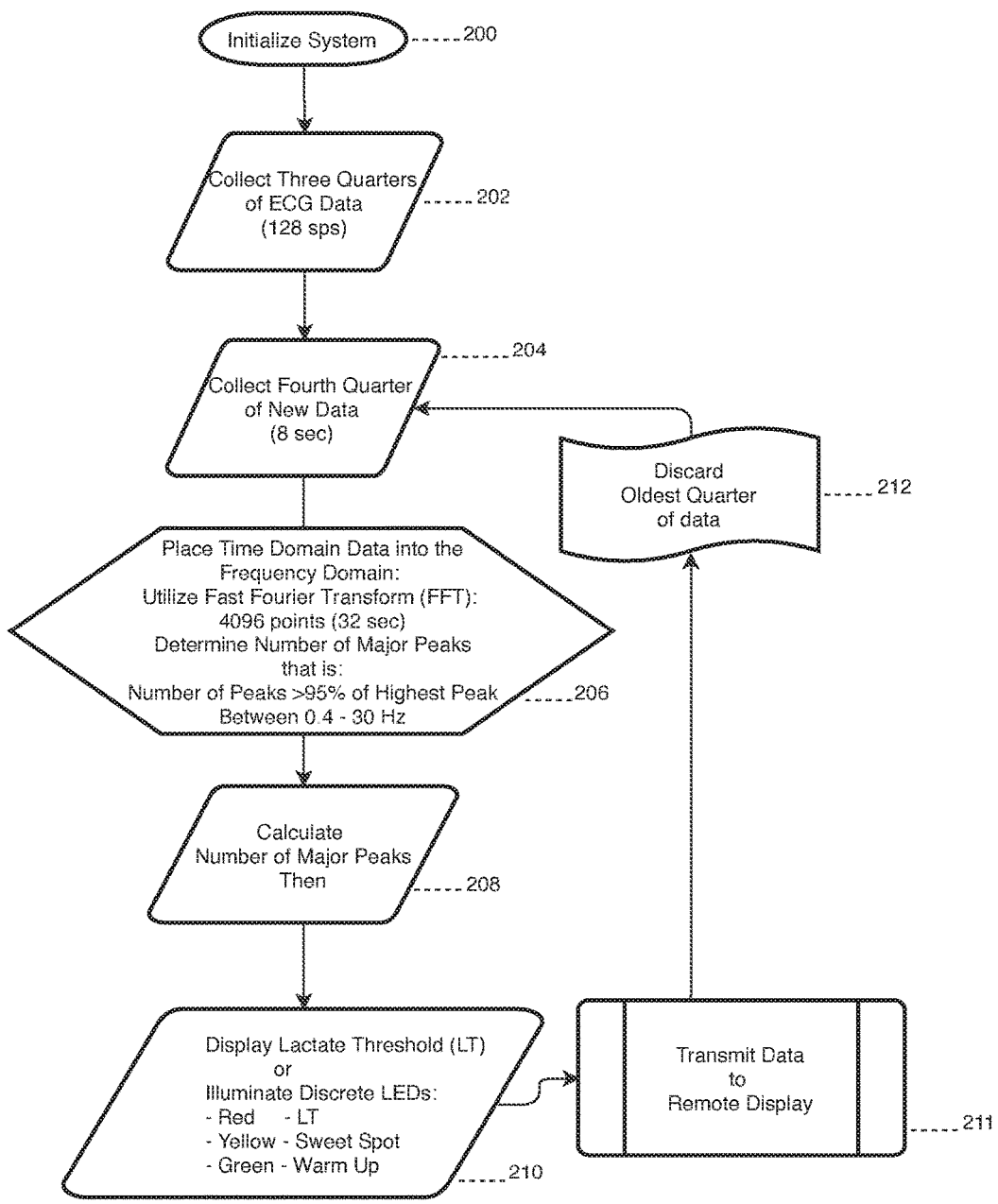
FIG. 1 is a flow chart illustrating the algorithm used by the second signal analyzer, that is, an exemplary process of the digital signal processing method utilizing FFT-based spectral analysis for calculating lactate threshold by detecting and counting the number of major peaks representing the fundamental cardiac and harmonic cardiac spectral lines, as well as their satellite spectral lines caused by heart rate variability.

In the following detailed description, reference is made to the accompanying drawings, which form part of the present disclosure. The embodiments described in the drawings and description are intended to be exemplary and not limiting. As used herein, the term "exemplary" means "serving as an example or illustration", and should not necessarily be construed as preferred or advantageous over other embodiments. Other embodiments may be utilized and modifications may be made without departing from the spirit or the scope of the subject matter presented herein. Aspects of the disclosure, as described and illustrated herein, can be arranged, combined, and designed in a variety of different configurations, all of which are explicitly contemplated and form part of this disclosure. For example, the first signal analyzer and second signal analyzer may be combined into a unified signal analyzer in another embodiment.

Described herein are illustrative embodiments for methods and systems for a wearable lactate threshold exercise device (LTD). In representative embodiments, an LTD non-invasively and directly measures Heart Rate (HR), Heart Rate Variability (HRV), number of major fundamental cardiac, harmonic cardiac, and satellite heart rate variability peaks (MP), and detects Lactate Threshold (LT). These parameters taken together provide important and key information regarding Lactate Threshold (LT), which can thus be effectively used in the prescription of heavy exercise, which may alternate between aerobic and anaerobic physiologic exercise zones (well known to those skilled in the art), and include the real-time calculation of user-specific heart rate exercise zones and cycling/running power exercise zones. These variables can thus be effectively used as a tool to improve the efficiency of heavy exercise and increase calorie burn through visual feedback on a local or remote display.

Further, HR, HRV, and Serum Lactate Concentration variables are well known and are common independent measures in clinical, hospital, and critical care settings, and during exercise. However, measuring these variables in real-time in the field while undergoing heavy exercise is much more difficult and challenging than measuring them in clinical or laboratory settings. In fact, accurate, reliable, and reproducible measurement of the entire variable group (HR, HRV, Lactate Threshold) solely from the electrocardiogram has not yet been accomplished in real-time during outdoor exercise in the field. The LTD embodiments described herein utilizes three important principles in order to make the device work in the field in real-time under HEAVY exercise conditions: (i) portable and wearable; (ii) digital signal processing via FFT-based spectral analysis; and, (iii) wireless telemetry to a local and/or remote display. This combination of features is considered essential by coaches, trainers, experts, and athletes themselves in order to optimize the prescription of heavy exercise in real-time, and thus improve competitive ability and increase calorie burn.

Two key concepts for Lactate Threshold (LT) measurement are that core body temperature (Tcore) rises, and blood pH decreases, sometimes dramatically, when lactate threshold is reached, and continued HEAVY exercise thereafter may proceed beyond LT into the anaerobic realm, if not carefully monitored and coached. For example, Tcore may change from 37° C. (normal) towards 41° C. (hyperthermia), and blood pH may drop from 7.40 (normal) towards 7.10 (acidemia), when LT is reached. As these changes occur, individual muscles, the cardiovascular system, and the central nervous system may become markedly less efficient, especially if LT exercise is not practiced often, or the exercising subject proceed beyond LT into the anaerobic realm.

LTD embodiments described herein detect lactate threshold in the exercising athlete, in the field, by digital signal processing of the electrocardiogram, using fast fourier transform (FFT) based spectral analysis, indirectly estimating decreasing blood pH and increasing blood lactate levels, thus accurately detecting the presence of Aerobic Exercise, Lactate Threshold, and Anaerobic Exercise, in real-time. Heart Rate Exercise Zones and Cycling/Running Power-based Exercise Zones may be individualized, in real-time, based upon electrocardiogram-based lactate threshold detection. Non-invasive lactate threshold monitoring by the LTD makes prescription of HEAVY exercise by trainers and coaches more precise and productive. For example, an LTD may effectively be utilized for the prescription of high intensity interval training (HIIT) and Tabata Intervals, or to increase the amount of calorie burn over shorter intervals of training time.

It is now clear by those skilled in the art through decades of research that LT is a critical exercise transition period representing the level of physical performance at which muscles just begin to produce more lactic acid than can be removed by liver and muscle enzyme systems. As LT is reached, maximal exertion becomes limited. Continued exertion significantly above LT into the anaerobic realm can last for only a few more minutes, as oxygen debt, hyperthermia, and lactate acid build up into the muscles, typically causing the central nervous system to communicate emphatically to the exercising subject a clear and present message of fatigue, and to stop and rest as soon as possible.

Lactate threshold (LT) is a useful measure for deciding exercise intensity for training and racing, and to significantly increase calorie burn. LT varies significantly between individuals depending on athletic fitness, and LT can be markedly increased with training and coaching. High intensity interval training (H.I.I.T) takes advantage of the body being able to temporarily exceed the lactate threshold, and then recover (reduce blood lactate concentration) while operating below the threshold and while still doing physical activity. Fartlek, Tabata, and H.I.I.T are similar forms of interval training, the main difference being the structure of the exercise. Interval training can take the form of many different types of exercise, and most coaches and trainers attempt to closely replicate the movements found in the desired sport being played by the exercising subject.

Within competition, LT has assumed a central role in real-time decision making for athletes and coaches ranging from Olympians to 'age-groupers' in triathlons. Precisely knowing the LT limit can be a key influence to guiding intra-race decisions, say to either accelerate and 'go with' a competitor who passes on the right, or simply 'stay put and hold tight' at the current race pace.

However, the ability to measure LT and provide this parameter to athletes is typically available only through the service of indoor, stationary, exercise physiology laboratories with bulky non-portable machinery. For example, the gold standard for determining LT involves repeated sampling of blood via finger or ear needle pricks for blood lactate analysis. This gold-standard LT detection procedure is time consuming, expensive, uncomfortable, has innate infection control issues, has built-in time delays, and is especially inconvenient in the HEAVY exercising athlete. Other prior art non-invasive LT testing methods are equally inconvenient and require additional and unwieldy apparatus worn on the face, head, and/or legs, for measurement of respiratory gas exchange, and/or infrared optical analysis, either one of which methods are difficult to analyze outdoors in the field, due to their size, weight, motion artifact, and/or sunlight interference issues.

In contrast, the exemplary embodiments described herein non-invasively makes LT available to athletes, in the field, in real-time, during their work-out period, through electrocardiogram monitoring, and FFT-based spectral analysis. It is well known to those skilled in the art that at the point of LT, lactate concentration increases from the anaerobic metabolism of glucose. Lactate is buffered in the blood, pH begins to decrease, sympathetic nervous system activity increases (i.e. 'fight or flight'), and parasympathetic nervous system activity decreases (i.e. 'respiratory sinus arrhythmia'). In essence, at lactate threshold, any changes due to heart rate variability in the electrocardiogram reach a minima, as the autonomic nervous system activity becomes saturated.

In one embodiment, the specified LTD monitors primarily for a significant decrease and resultant minima in the number of major peaks (MP, that is, number of fundamental cardiac, harmonic cardiac, and satellite heart rate variability spectral lines) between 0.4 and 30 Hz in the electrocardiogram frequency spectrum. Lactate Threshold is detected through FFT-based spectral analysis, in real-time, and thus provides for a portable, easy, and inexpensive way to detect LT in the field by athletes and coaches alike, providing instantaneous feedback via local and/or remote display of the results. Particular variable combinations may then be useful to better define and refine heart-rate-based and/or power-based training zones, and control training intensity, in preparation for a major competition event, or to increase weight loss.

Figure 6:
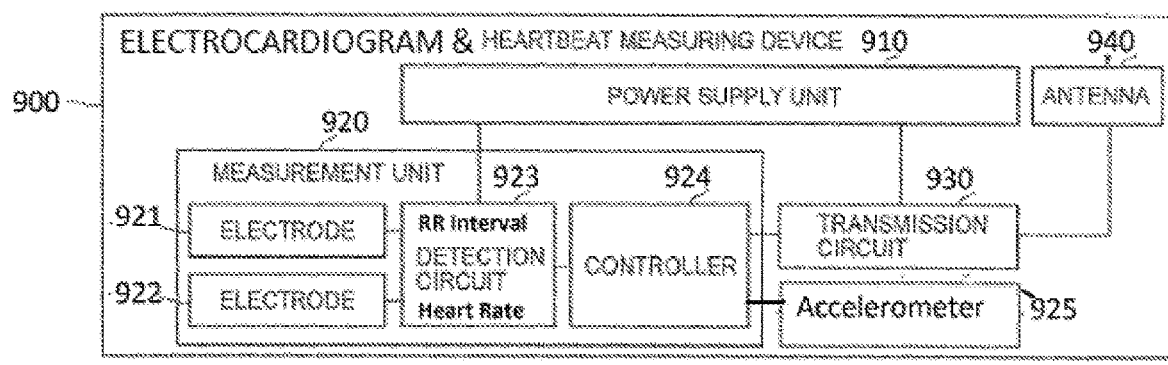
FIG. 6 is a block diagram of the electrocardiogram-based chest belt apparatus utilized as a wearable lactate threshold device (LTD) in accordance with an illustrative embodiment. Note this chest belt monitoring device has a first signal analyzer which gathers the electrocardiogram from the sensors, conditions and digitizes the electrocardiogram data, then telemeters the data to the second signal analyzer. In some embodiments, the chest belt may also have an accelerometer to detect characteristic movements associated with heavy exercise, although the presence of an accelerometer is not essential to the function of the LTD.

As shown in FIG. 6, the exercise chest belt apparatus detects the electrocardiogram with two electrodes, a detection circuit, a controller (that is, a first signal analyzer), and a telemeter with a transmission circuit and an antennae. The controller 924 may be any computer system capable of collecting, conditioning, and digitizing an analog electrocardiogram signal from the electrodes, accurately counting the R-R interval to determine instantaneous heart rate, and telemetering the digitized data on through the transmission circuit and antennae to the second signal analyzer.

Figure 2:
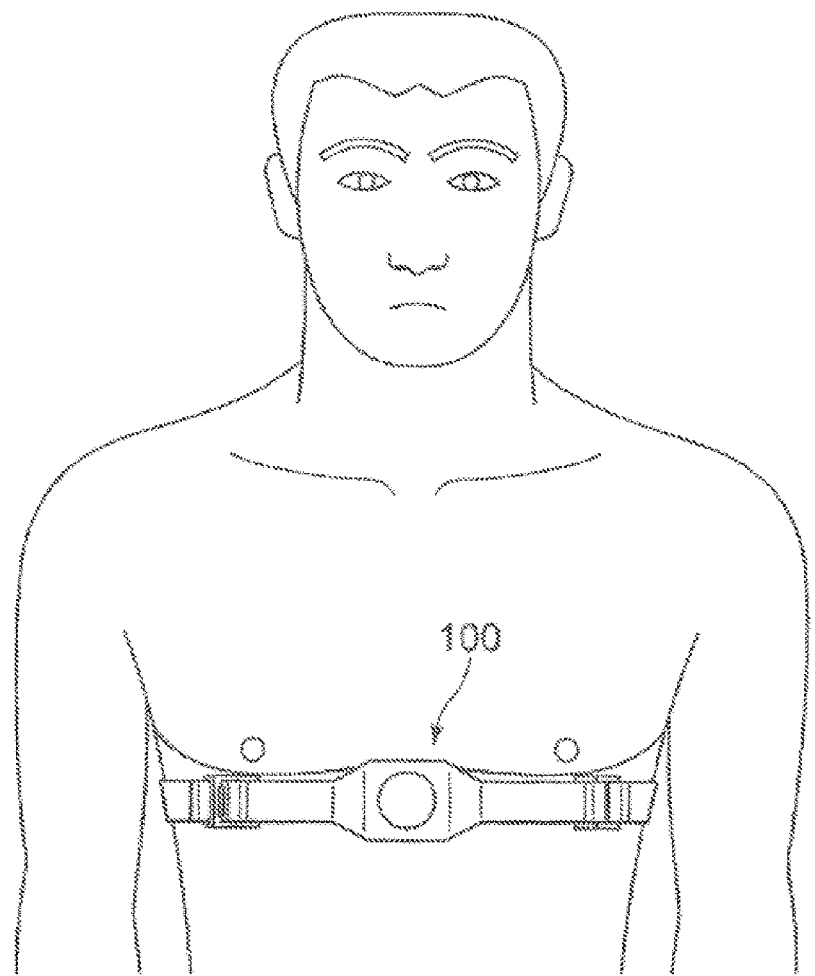
FIG. 2 is an electrocardiogram-based chest belt apparatus utilized as a wearable lactate threshold device (LTD) in accordance with an illustrative embodiment, which contains the first signal analyzer for gathering the electrocardiogram from the sensors, conditioning and digitizing the signal, before telemetering the digitized data to the second signal analyzer for further processing.
Figure 3:
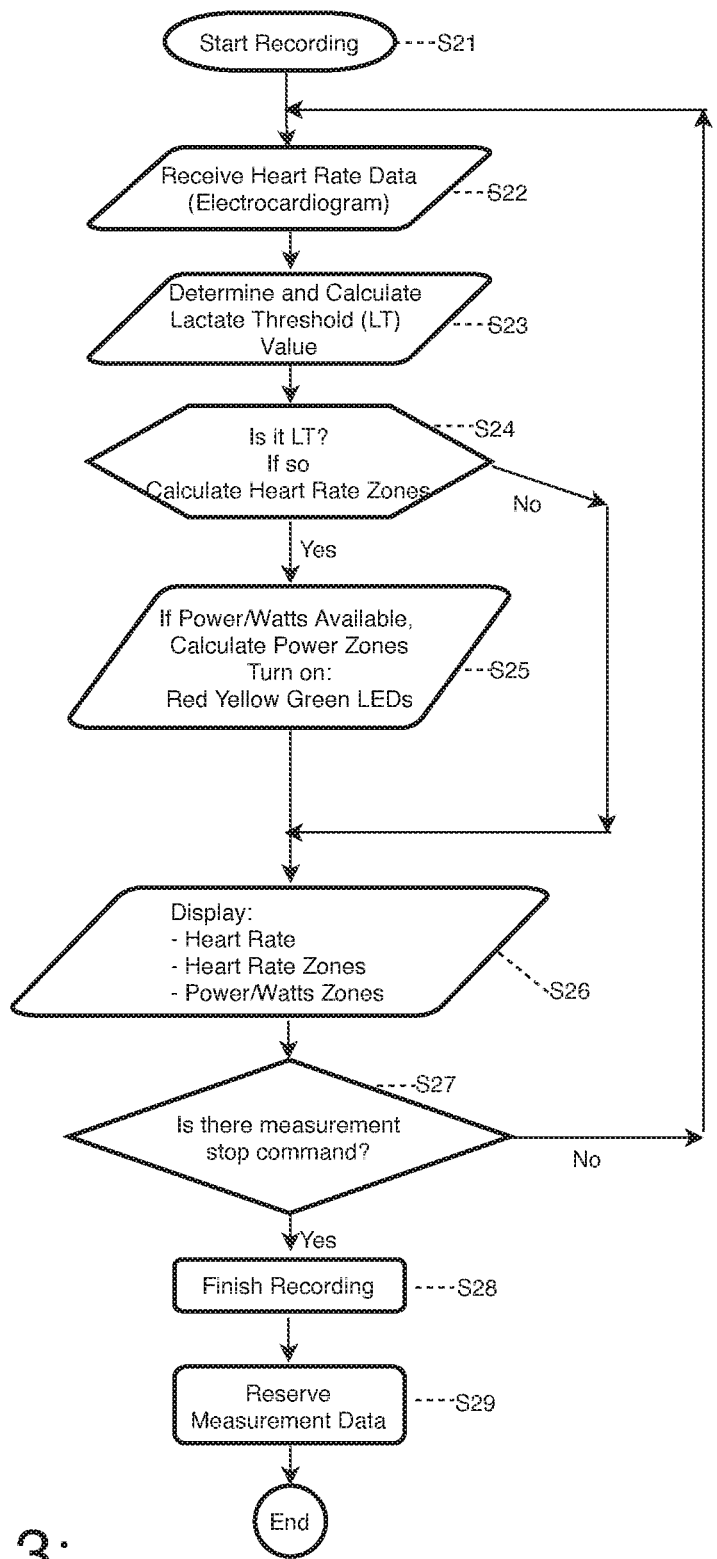
FIG. 3 is a system diagram of the second signal analyzer which receives electrocardiogram and heart rate information from the first signal analyzer and telemeter in the chest belt apparatus. The second signal analyzer utilizes an FFT-based spectral analysis method, then finally displays measurement data such as instantaneous heart rate, average heart rate, heart rate (in beats per minute) at Lactate Threshold, Cycling/Running power (in Watts) at Lactate Threshold, and Heart Rate Exercise Zones as well as Cycling/Running power exercise zones, in accordance with an illustrative embodiment.

In some embodiments, the controller 924 may include a CPU, random access memory (RAM), and read-only flash memory (ROM). Further, the controller 924 is the first signal analyzer. For example, the MAX30003 controller (Maxim Integrated, San Jose, Calif.) is a complete, biopotential, analog front-end solution for a wearable electrocardiogram chest belt which is ultra-low power for long battery life. The MAX30003 has a single biopotential channel providing ECG waveforms and instantaneous heart rate detection, and has electrostatic device protection, electro-mechanical interference filtering, internal lead biasing, direct-current leads-off detection, and ultra-low power leads-on detection during standby mode. The MAX30003 biopotential channel has high input impedance, low noise, high common mode rejection ratio, programmable gain, low-pass and high-pass filters, high-resolution analog-to-digital converter, is direct current coupled, and can handle large electrode voltage offsets. The MAX30003 is a microchip available in a 28-pin Thin Quad Flat No Leads Package (TQFN), and can easily fit onto a small printed circuit board which fits into the chest belt apparatus pod 100, as shown in FIG. 2.

After the digitized electrocardiogram data is telemetered from the chest belt apparatus pod 100 to the second signal analyzer, as shown in FIG. 1, the digitized data are converted into the frequency domain by performing the well-known Fast Fourier Transform (FFT). In other embodiments, other common techniques of converting time-domain data to the frequency domain may be used: e.g., discrete cosine transform, wavelet transform, discrete Hartley transform, Gabor transform, Auto-regressive (AR) Spectral Estimation, and the Lomb-Scargle (LS) periodogram.

Figure 4:
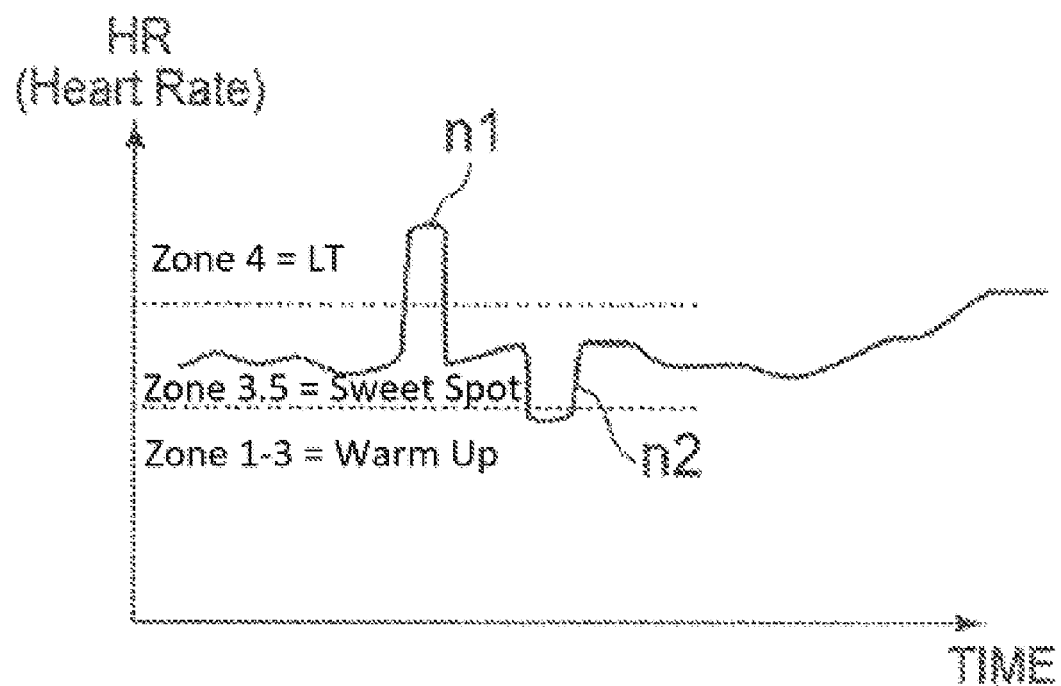
FIG. 4 is the local or remote smartphone or smartwatch display which features the electrocardiogram and lactate threshold data as calculated by the first and second signal analyzers. The second signal analyzer utilizes an FFT-based spectral analysis method to display measurement data such as instantaneous heart rate, average heart rate, heart rate (in beats per minute) at Lactate Threshold, and Heart Rate Exercise Zones 1-5, and Cyling/Running Power Zones, which are well known to those skilled in the art, in accordance with an illustrative embodiment.
Figure 5:
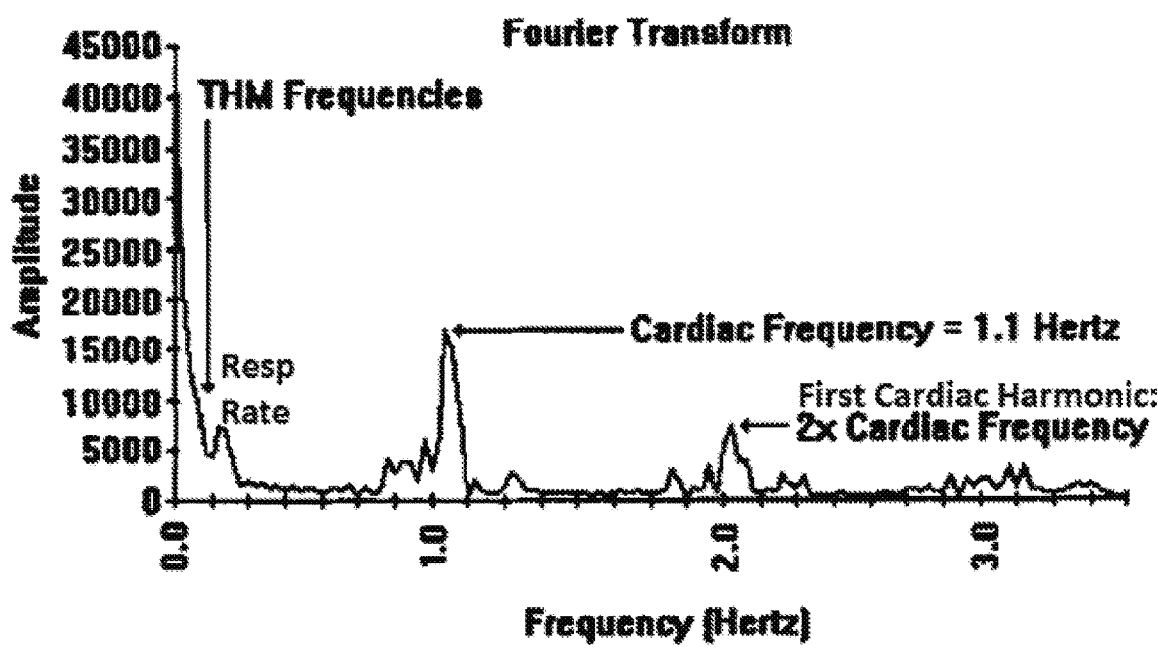
FIG. 5 is an exemplary process of the digital signal processing method utilized by the second signal analyzer. The second signal analyzer utilizes an algorithm for FFT-based spectral analysis of the electrocardiogram. In the example shown in this figure, the subject is at rest. Shown in the frequency domain are the characteristic spectral lines representing fundamental cardiac, respiratory, and THM spectral lines, as well as cardiac harmonic spectral lines, and their satellite spectral lines caused by heart rate variability, which are well known to those skilled in the art, in accordance with an illustrative embodiment.

The frequency domain data may then be analyzed to determine the instantaneous and average heart rate, HRV, heart rate at lactate threshold, and cycling/running power at lactate threshold. Based upon the real-time analysis of lactate threshold, the exercising subject's exercise heart rate zones and cycling/running power zones are also calculated in real-time, and displayed on a local or remote smartwatch and/or smartphone display, as shown in FIG. 4.

In other embodiments, a suitable computer system for digital signal processing other than a smartphone and smartwatch may be used, for example a personal computer operating system, such as Microsoft Windows, MacOS, or Linux, with suitable display.

As shown in FIG. 6, the transmission circuit 930 and antenna 940 telemeter the data wirelessly from the first signal analyzer to the second signal analyzer, and onto a local or remote display, typically on a smartwatch or smartphone. The transmission circuit 930 and the antenna 940 may be any suitable radio frequency or other wireless telemetry system. These telemetry systems are well known to those skilled in the art, and are widely available. Bluetooth and WiFi telemetry protocols may be used to allow highly secure and noise-immune telemetry of desired electrocardiogram values and variables, even in HEAVY exercise environments. In one embodiment, multi-protocol bluetooth 4.x low energy, 2.4 GHz, radiofrequency (RF), system-on-a-chip (SoC), technology provides a highly secure link, high noise immunity, and high informational capacity, to transmit the electrocardiogram data from the first signal analyzer to the second signal analyzer. These telemetry traits are highly desirable in the wearable exercise device environment. In alternative embodiments, transmission circuit 930 may telemeter data via Bluetooth Classic or Wifi Direct data streams, from the first signal analyzer to the second signal analyzer, and for local or remote display on either smartphones or smartwatches, as well as to any personal computer with a Bluetooth or Wifi connection.

Once the values are calculated and telemetered using transmission circuit 930, the values calculated by the second signal analyzer may be displayed to an observer (including self) on a local or remote display. In some embodiments, the local or remote display may be a smartphone or smartwatch, as shown in FIG. 4.

The local and remote displays may display information about the detected and analyzed electrocardiogram data. For example, the display may be any display capable of displaying one or more heart rate, HRV, lactate threshold, heart rate zones, and cycling/running power zones to the desired resolution. Liquid crystal display (LCD) and organic light-emitting-diode (OLED) are display technologies well known to those skilled in the art, and ideal for certain embodiments of the LTD. In addition, a stack of discrete LEDs, or tricolor LED(s), may be used if the designer desires to display binary, tertiary, or logarithmic variable values. In an alternative embodiment, green, yellow, and red discrete LEDs, or a tricolor LED, or color stripes on an LCD or OLED screen, may be configured to represent baseline, approaching, and desired conditions corresponding to lactate threshold, exercise heart rate zones, and cycling/running power zones, during HEAVY exercise.

Some embodiments may provide a complete system-on-a-chip (SOC) solution utilizing a controller 924 wherein the first signal analyzer and second signal analyzer are combined into a unified signal analyzer, wherein the time-domain electrocardiogram data may be converted into the frequency domain by a hardware floating point unit (FPU) via FFT-based spectral analysis. The SOC is portable, low-power, wireless, real-time device, with signal analyzer capable of using FFT-based spectral analysis, which analyzes lactate threshold and telemeters the variable results to an exercising subject or observer with local or remote display. The unified signal analyzer may be a floating point unit (FPU) integrated with the controller 924. Thus, an extremely small device can be constructed to fit into the chest belt pod 100 for real-time use in the field under HEAVY exercise conditions.

The size and positioning of the LTD 100 may allow for it to be used during various activities. Thus, whether running on the track, cycling on the road, or swimming in the pool, athletes can see what is happening during HEAVY exercise on a local or remote display, and potentially manipulate their exercise intensity as they approach and breakthrough LT, back and forth through the aerobic and anaerobic exercise zones. For example, LT may be approached but not crossed over in a time-trial competitive race event in order to utilize energy most efficiently. On the other hand, LT may be broken through programmatically during high intensity interval training for maximal training benefit and maximum calorie burn. With this information in hand, athletes, trainers and coaches can measure and improve work output more precisely, maximize weight loss strategies, and thus improve overall training regimens and competitive ability.

Importantly, embodiments of the LTD 100 are able to resolve all size and battery power issues through a minimal microchip design philosophy: one-microchip for electrocardiogram detection and conditioning, with serial data stream telemetering via an equally small microchip, or combining the microchips into one system-on-a-chip (SOC). In this manner, the LTD 100 may efficiently and portably calculate the desired lactate threshold in the field in real-time under HEAVY exercise conditions.

Heart Rate Variability (HRV) is the physiological phenomenon of variation in the time interval between heartbeats. It is measured by the variation in the beat-to-beat intervals where R is a point corresponding to the peak of the QRS complex of the electrocardiogram (ECG) wave. Thus, HRV as measured in the time domain is the standard deviation or root mean square of the differences between successive R-R intervals or instantaneous heart rates. Other methods in the time domain known to those skilled in the art to detect heart beats and their variation include: blood pressure and the optical pulse wave signal reflected or transmitted through the skin known as the photo-plethysmogram (PPG) or pulse oximetry. Importantly, ECG is considered a superior method because it provides a clear, accurate, and precise QRS waveform, most immune to motion artifact due to its high signal to noise ratio, which makes it easier to analyze, and exclude heartbeats not originating in the sinoatrial node of the heart electrical system. Most importantly, the LTD does not utilize a time domain method to detect heart rate variability, but instead uses a novel frequency domain algorithm described herein to most precisely and accurately detect key changes in heart rate variability seen at lactate threshold.

HRV is related to autonomic nervous system activity. The main inputs are from the sympathetic (SNS) nervous system, parasympathetic nervous system (PSNS), and humoral factors. Respiration gives rise to waves in heart rate mediated primarily via the PSNS, called respiratory sinus arrhythmia (RSA), and during exercise may be found in the 0.15-1.00 Hz range. SNS activity represents Traube-Hering-Mayer (THM) waves in the 0.03-0.15 Hz range. Factors that affect the THM and RSA waves are the baroreflex, thermoregulation, hormones, sleep-wake cycle, meals, physical activity, HEAVY exercise, and stress.

There are two primary LF-THM and HF-RSA fluctuations:

(1) High-frequency oscillations are caused by a heart rate variation associated with respiratory sinus arrhythmia (HF-RSA), which faithfully tracks the respiratory rate across a range of frequencies (0.15-0.40 Hz, and then up to 1.00 Hz during HEAVY exercise, or about a 4-second period);

(2) Low-frequency oscillations are caused by a heart rate variation associated with Traube-Hering-Mayer (LF-THM) waves in the range of 0.03-0.15 Hz, or about a 10-second period.

Both autonomic nervous system and respiratory system activity are present in physiologic waveforms, certainly including the electrocardiogram (ECG). During HEAVY exercise, both low frequency (LF) THM waves (0.03-0.15 Hz) and high-frequency (HF) RSA are decreased, representing decreased PSNS activity and increased SNS activity. Notably, during HEAVY exercise, HRV at Lactate Threshold (LT) will be at a minima, which is detected by the LTD in the frequency domain as a minima in the number of major peaks (MP).

This embodiment of the LTD 100 converts electrocardiogram (ECG) data from the time-domain to the frequency domain using FFT-based spectral analysis. This frequency domain method, never before utilized in exercise devices in the field in real-time, assigns bands of frequency and then counts the intensity of HRV that matches each band. The HRV bands for analysis are low frequency (LF-THM) from 0.03 to 0.15 Hz, high frequency (HF-RSA) from 0.15 to 1.0 Hz, and, most importantly during HEAVY exercise, from 0.40 to 30.00 Hz, in order to count the number of major peaks (MP) associated with the cardiac fundamental, cardiac harmonic, and satellite heart rate variability spectral lines. Since HRV is at a minima at Lactate Threshold (LT), it follows that the number of major peaks (MP) will be at a minima at LT as well, which is the fundamental physiologic basis for the LTD, and what is completely novel in the current invention.

For example, in certain embodiments, the LTD 100 telemeters electrocardiogram data from the first signal analyzer to the second signal analyzer, transforms the ECG data from the time domain to the frequency domain utilizing the fast fourier transform (FFT), and calculates power spectral density (PSD) spectral lines for each frequency band. In an alternative embodiment, autoregressive (AR) spectral estimation is utilized. The FFT method is preferred and offers: (1) simplicity of the algorithm; and, (2) high processing speed. In the alternative embodiment, the advantages of AR are: (1) smoother spectral components that can be distinguished independent of preselected frequency bands; (2) easy post-processing of the spectrum with an automatic calculation of low- and high-frequency power components with an easy identification of the central frequency of each component; and, (3) an accurate estimation of PSD even on a small number of samples on which the signal is supposed to maintain stationarity.

For appropriate electrocardiogram-based cardiac spectral line analysis, for fundamental, harmonic, and satellite frequencies, for best FFT accuracy and precision, certain embodiments may acquire a data window of approximately one half to one full minute, recognizing the lowest bound of HF-RSA is 0.15 Hz (6.3 cycles/min); while the lowest bound of LF-THM component is 0.03 Hz (1.8 cycles/min).

Although cardiac automaticity is intrinsic to various pacemaker tissues, heart rate and rhythm are largely under the control of the autonomic nervous system. The parasympathetic influence on heart rate is mediated via release of acetylcholine by the vagus nerve. The sympathetic influence on heart rate is mediated by release of epinephrine and norepinephrine. Under resting conditions, vagal tone prevails and variations in heart period are largely dependent on vagal modulation. However, it is important to note that vagal and sympathetic activity constantly interact with each other.

HRV present during resting conditions represent beat-by-beat variations in cardiac autonomic inputs. Efferent vagal (parasympathetic) activity is a major contributor to the HF-RSA component. The LF-THM component is mainly a marker of sympathetic modulation, but may also represent both sympathetic and vagal influences. For example, during sympathetic activation the resulting tachycardia is usually accompanied by a marked reduction in total FFT power at the HF-RSA and LF-THM spectral lines.

It is important to note that HRV measures fluctuations in autonomic inputs to the heart, rather than the mean level of autonomic inputs. Thus, both withdrawal and saturating high levels of autonomic input to the heart can lead to markedly diminished HRV in the electrocardiogram during HEAVY exercise.

Monitoring exercise training using an LTD 100 with an electrocardiogram chest belt may decrease cardiovascular mortality and sudden cardiac death. Regular exercise training is thought to modify cardiac autonomic control favorably. For example, Individuals who exercise regularly have a 'training bradycardia' (i.e., low resting heart rate) and generally have higher HRV during rest periods than sedentary individuals.

As shown, in one embodiment, the monitoring device 100 and transmission circuit 930 may be packaged in a single printed circuit board with a single battery power supply unit 910. The chest belt electrodes 921, 922 may be placed in electrical communication with the skin and the intravascular blood beneath in order to obtain an electrocardiogram signal, as is well known to those skilled in the art.

A well-known existing problem with typical usage of an exercise chest belt sub-system is the need or requirement to moisten the plastic or fabric heart rate sensor electrodes prior to use. To combat dry skin at the beginning of an exercise session, moisture is added to ensure better contact and adequate functioning of the device. When sweating commences, plastic sensor contacts will improve because the salt in sweat begins conducting the electrical signal. If the strap has fabric electrodes, it is essential that the sensors are moistened thoroughly with water before exercise.

Regardless of the need to moisten the sensors, any chest belt sub-system needs appropriate tightening of the elastic strap. If the strap is loose, the movement of the electrodes will disturb ECG signal detection. For best signal acquisition, the elastic belt is initially placed right under the pectoral muscles, but may be adjusted so the sensors are placed onto the mid-back to produce high fidelity ECG signals as well.

One final problem is chest hair may weaken electrode sensor contact areas. The best solution to this issue for existing chest belt sub-systems is to shave a small area on the chest wall so the sensors make better contact, resulting in better conductivity and better ECG signal fidelity.

The main problem with existing exercise chest belt electrodes is that they require skin preparation, conduction gel, or sweat during exercise to reduce the skin-electrode interface impedance. This problem not uncommonly causes trouble to users, as they are unable to test chest belt function while at rest, prior to exercise. Also, the addition of conduction gels may leave residue on the chest wall skin or cause short circuit between two electrodes in close proximity. Moreover, these aforementioned preparation procedures are time consuming and uncomfortable, since the skin preparation may involve abrasion of the outer skin layer and/or clipping of the chest hair.

In an alternate embodiment, dry foam electrodes within the exercise chest belt sub-system exhibits electrically conductive polymer foam and fabric, and provides strong capacitive behavior at the chest wall and skin interface points. The electrically conductive polymer foam substrate within the dry electrodes fit the chest wall surface and increase the contact area between skin and electrode, and, as a result, reduce the impedance. The foam-skin interface is not only used to reduce the motion force, but also used to increase the fabric-skin contact area when force is applied on the electrode. The foam will also assimilate the motion force, preventing rubbing and sliding of the electrode on the skin, thus simultaneously reducing the motion artifact and skin-electrode interface impedance.

In this alternate embodiment, E103/HART/Polyester and E103/HART/XAC/Polyethylene are both effective rigid ECG electrically conductive polymer foams with open and closed pores, respectively. Dry foam electrodes may also be covered by a conductive fabric. The somewhat rigid edges of the foam slightly scratch and abrade the skin and thus gently reduce the skin impedance. These unique foam properties make the previously standard preparation of shaving chest hair unnecessary. In addition, these dry foam electrodes are much more resistant to motion artifact, such as that typically produced during HEAVY exercise when using chest belts with plastic or fabric electrodes.

The smartphone/smartwatch-based second signal analyzer sub-system shown in FIG. 1 and FIG. 4 may utilize FFT-based spectral analysis to transfer the telemetered electrocardiogram signal from the time domain to the frequency domain. The calculated heart rate, HRV, and LT variables may be shown on a local or remote display sub-system on an observer or carried by a coach or trainer.

In one embodiment, the antenna 940 may be positioned within the chest belt, which can wrap around or otherwise encircle the chest anatomy to secure the package during HEAVY exercise. In an alternative embodiment, the antenna 940 may be positioned externally of the printed circuit board package, or the antenna may be embedded into the printed circuit board itself. In some embodiments, transmission may occur over Bluetooth, Wi-Fi, or other suitable wireless standard.

The local or remote display sub-system shown in FIG. 4 may be used to self-guide subjects in improving athletic performance in the field, and maximizing weight loss endeavors, through visual feedback. For example, the local or remote display may display when lactate threshold is reached, and utilize and display time spent in aerobic and anaerobic heart rate exercise zones as well as cycling/running power exercise zones.

In one embodiment, lactate threshold is detected through FFT-based spectral analysis of electrocardiogram during heavy exercise. FFT-based spectral analysis of electrocardiogram has not been used in real-time in the field before this current invention. HEAVY exercise causes progressive withdrawal of vagal activity, with key result being decreased fluctuations in heart rate variability from both HF-RSA and LF-THM spectral lines. This phenomenon may be calculated through FFT-based power spectral analysis by the second signal analyzer shown in FIG. 1 and FIG. 4. Therefore, lactate threshold may be determined through electrocardiogram spectral analysis by the second signal analyzer scanning for near complete withdrawal of the LF-THM and HF-RSA spectral lines during lactate threshold exercise. Importantly, the complete withdrawal of cardiac autonomic fluctuations during HEAVY exercise can most easily be determined when the number of major peaks of fundamental cardiac, harmonic cardiac, and satellite heart rate variability spectral lines reach a minima.

FIG. 1 is a flow diagram illustrating an exemplary process for calculating lactate threshold occurrence in accordance with an illustrative embodiment. In some embodiments, microcontroller firmware or smartphone/smartwatch software or personal computer system software may use these steps to calculate heart rate, HRV, number of major peaks of fundamental cardiac, harmonic cardiac, and satellite heart rate variability spectral lines, lactate threshold occurrence, heart rate exercise zones and cycling/running power exercise zones.

In one embodiment, three-quarters of the electrocardiogram data set are kept for processing for the next set of calculations by the second signal analyzer, with the oldest one-quarter of the data set removed, while the newest one-quarter of the data set is added. The data sets are converted from the time domain to the frequency domain by the fast fourier transform on a microcontroller with floating point unit, or by digital signal processing software on a smartwatch/smartphone sub-unit. The second signal analyzer picks and counts the correct number of major peaks (power spectral density and frequency) representing the fundamental cardiac, harmonic cardiac, and satellite heart rate variability spectral lines. The signal analyzer utilizes the power spectral data (PSD) and frequency bin data to further calculate the occurrence of lactate threshold by analyzing the real-time electrocardiogram data obtained during HEAVY exercise for the occurrence of a minima in the number of major peaks. Lactate threshold occurrence is subsequently displayed via yes-no box or with discrete red-yellow-green LEDs on a local or remote display to the observer or coach, as well as displaying more specific graphs of heart rate exercise zones and cycling/running power zones on a smartphone/smartwatch display.

In one embodiment, a microcontroller 924 first signal analyzer may initialize the system. Such initialization is very system-specific and is well known to those skilled in the art. After initializing the system, the microcontroller may begin collecting samples of electrocardiogram data at 128 samples per second. A "sample" is the reading of the magnitude and intensity values from the electrodes 921 and 922 of the chest belt.

When the electrocardiogram signal is being generated by the interaction of the electrodes with the skin, the detection circuit 923 and first signal analyzer generate a periodic electrical signal in the form of a digital serial pulse train corresponding to the intensity of the analog electrocardiogram signal. This digitized ECG signal may be interfaced into the microcontroller via 120 and SPI transfer, and an intensity value for the electrocardiogram signal is subsequently saved in random access memory (RAM).

In certain embodiments, the total collection period or FFT window is 32 seconds, which is divided into four quarters of approximately 8 seconds each. As shown in FIG. 1, three quarters (approximately 24 seconds) of data samples may be collected to help initialize a sliding window function. Next, the fourth quarter of the total sample (approximately 8 seconds worth of samples) may be taken. The sample rate and time of collection are all variable, and described here is just one embodiment. In this embodiment, between the samples taken, a total of 32 seconds or 4096 electrocardiogram data samples are collected for FFT processing. In alternative embodiments, the samples may be taken much faster from 256 Hz to 10000 Hz in order to satisfy the nyquist criteria, as is known to those skilled in the art, to prevent and minimize aliasing from electrical and optical interference, and implanted pacemaker signals.

Based on the electrocardiogram data sample, the system may determine the magnitudes and frequencies of the fundamental cardiac, harmonic cardiac, and satellite heart rate variability spectral lines, and count the number of major peaks (MP). That is, the 32 seconds of time-domain data is converted into the frequency domain by performing the well-known Fast Fourier Transform (FFT). The FFT may be performed in many ways, as is known to those skilled in the art. In one embodiment, an FFT of 4096 points (on data sampled at 128 Hz) will suffice.

Figure 7:
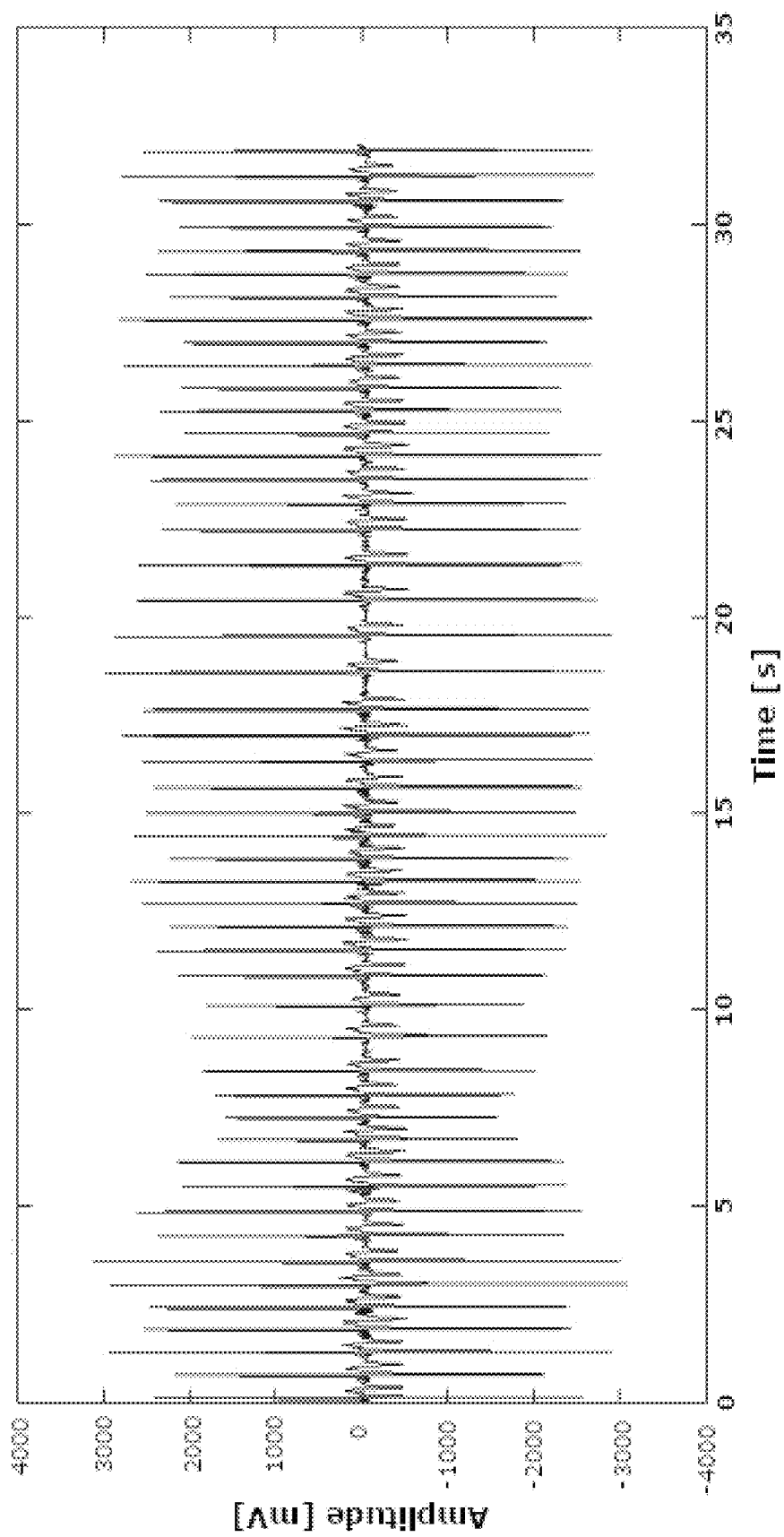
FIG. 7 is a time domain illustration of the electrocardiogram obtained from the chest belt apparatus utilized as a wearable lactate threshold device (LTD) in accordance with an exercise subject undergoing LIGHT exercise in an illustrative embodiment. Shown is the characteristic morphology of an electrocardiogram with P-QRS-T wave components and beat-to-beat variation caused by respiration and autonomic nervous system activity (heart rate variability), as is well known to those skilled in the art.
Figure 8:
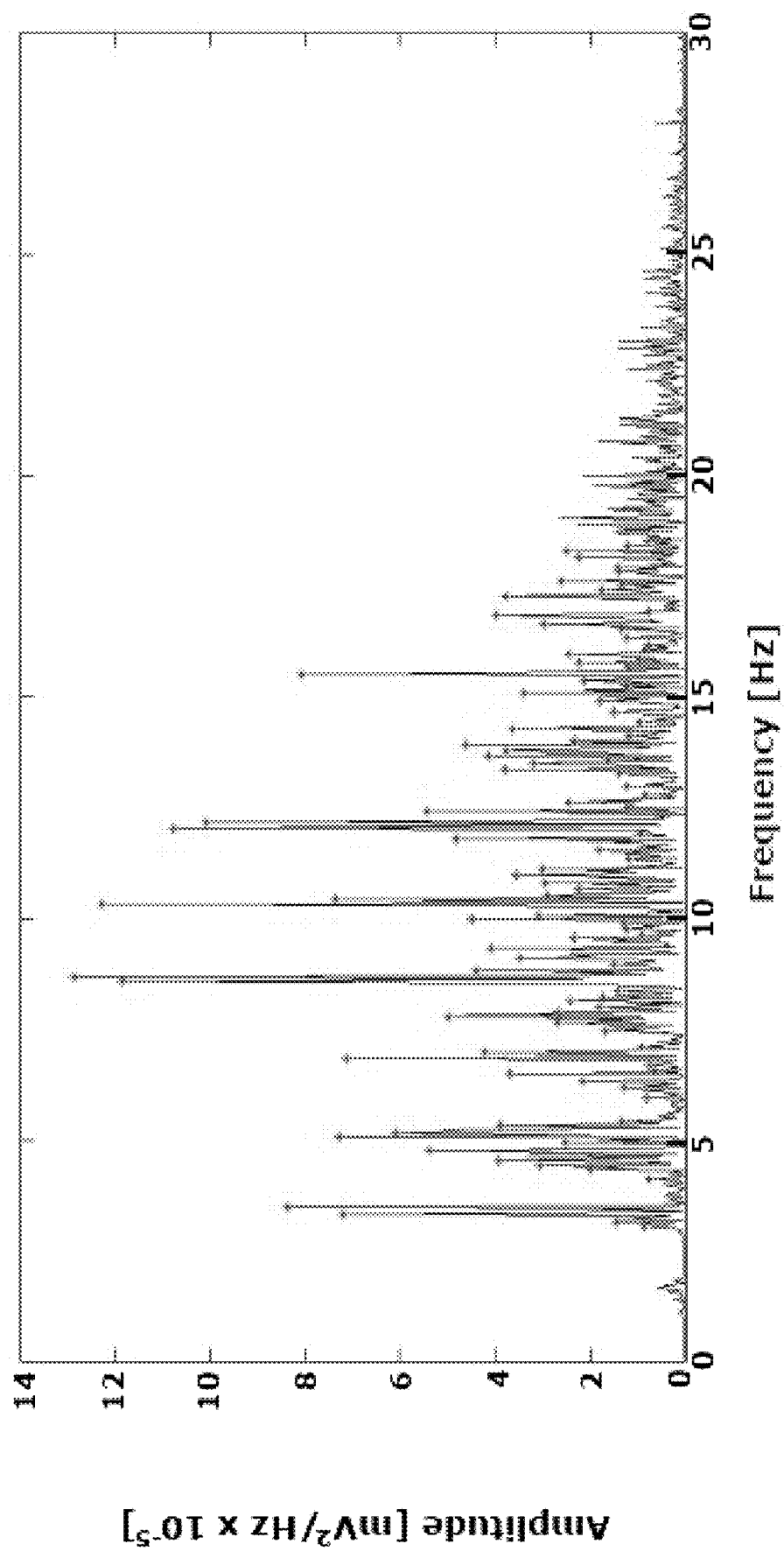
FIG. 8 is a frequency domain illustration of the electrocardiogram obtained from the chest belt apparatus utilized as a wearable lactate threshold device (LTD) in accordance with an exercise subject undergoing LIGHT exercise in an illustrative embodiment. Note the frequency domain data is made available in real-time after an FFT-based spectral analysis algorithm has been employed by second signal analyzer. Shown are the resultant key frequency components: fundamental cardiac, harmonic cardiac, and satellite heart rate variability spectral lines. The number and magnitude of spectral lines are calculated by the second signal analyzer as the NUMBER of MAJOR PEAKS, shown as >100 in this illustrative embodiment.
Figure 9:
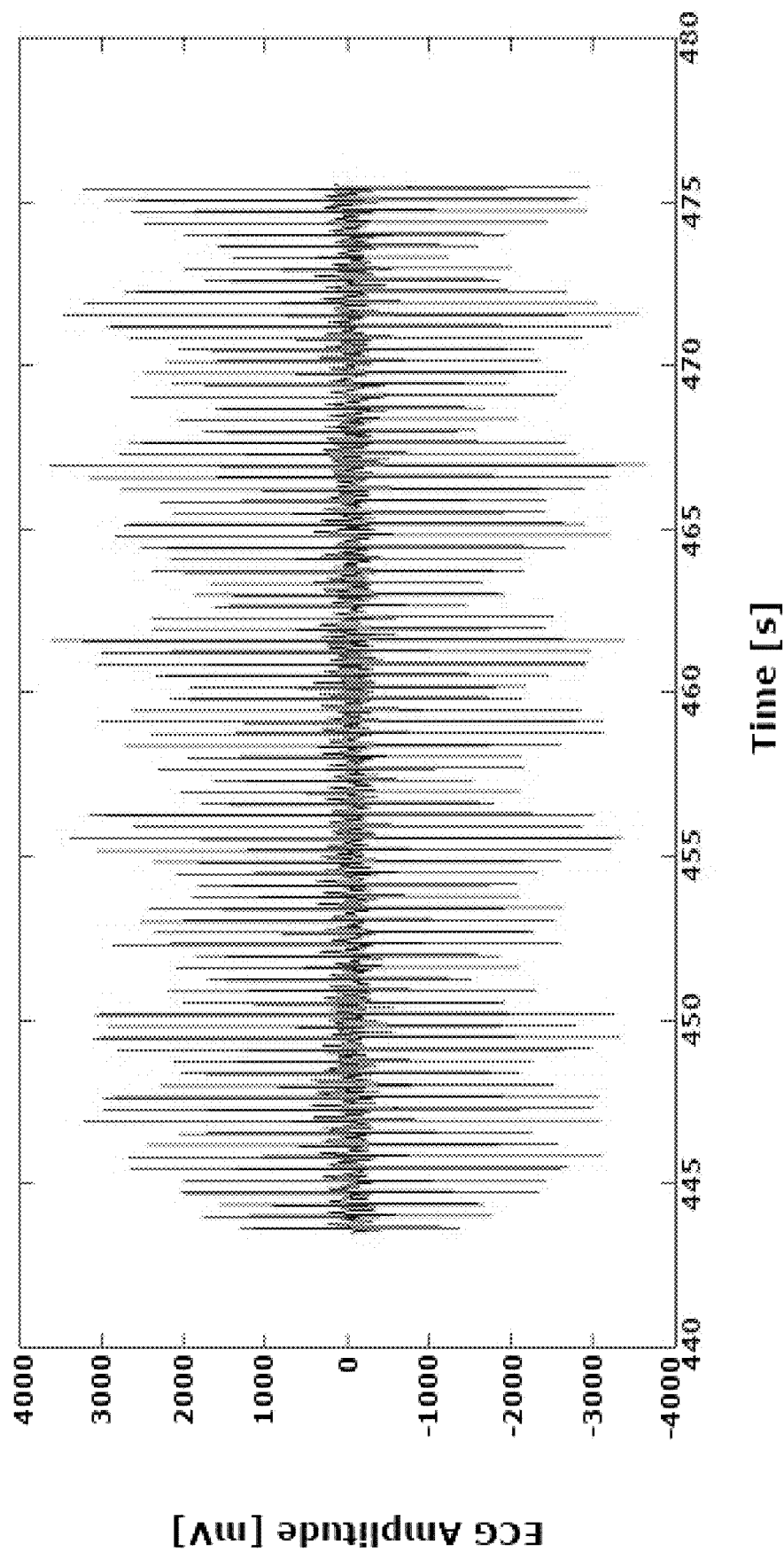
FIG. 9 is a time domain illustration of the electrocardiogram obtained from the chest belt apparatus utilized as a wearable lactate threshold device (LTD) in accordance with an exercise subject undergoing MEDIUM exercise, in an illustrative embodiment. Note the heart rate can easily be seen to be increasing with exercise activity.
Figure 10:
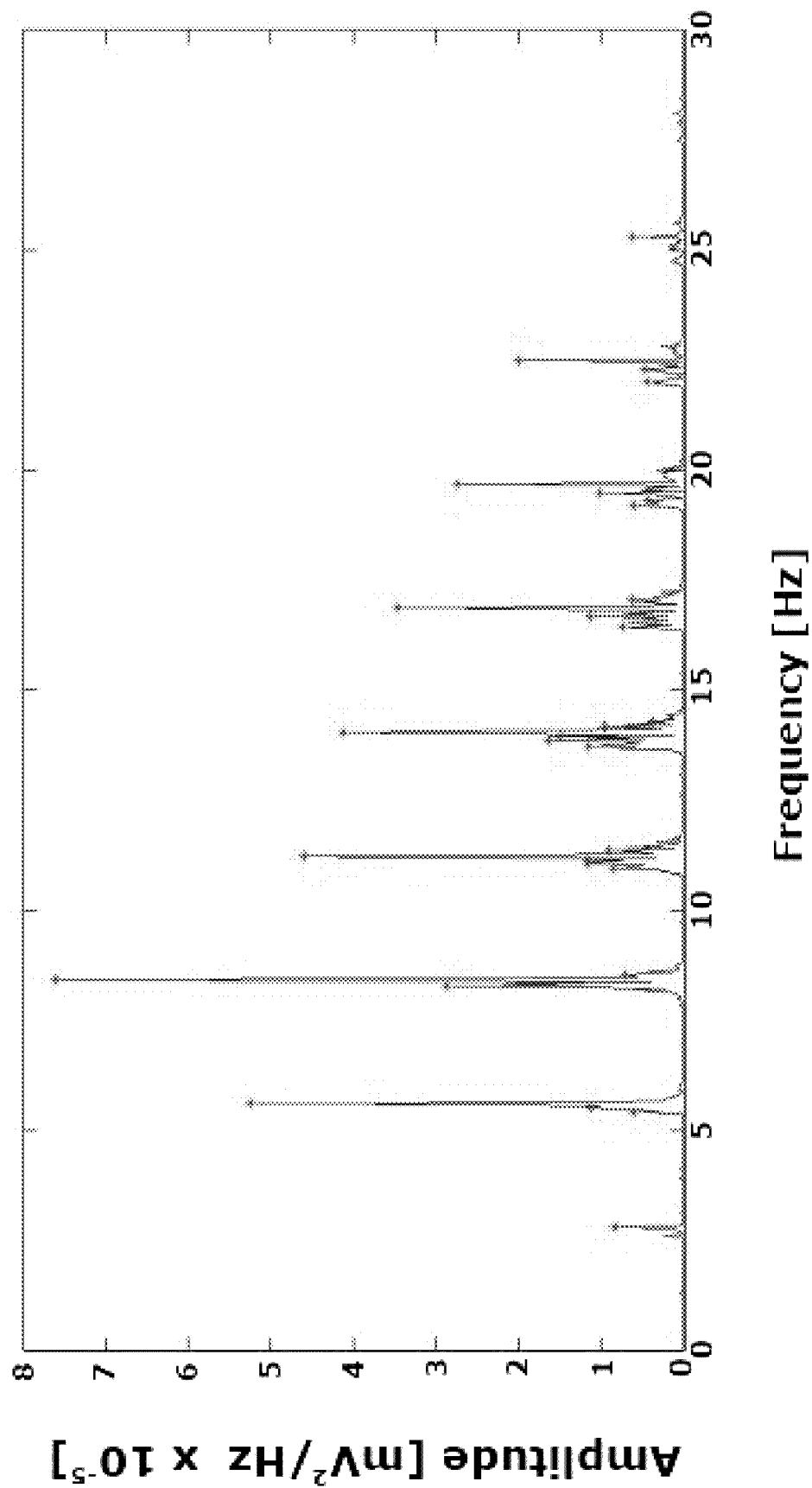
FIG. 10 is a frequency domain illustration of the electrocardiogram obtained from the chest belt apparatus utilized as a wearable lactate threshold device (LTD) in accordance with an exercise subject undergoing MEDIUM exercise in an illustrative embodiment. Note the frequency domain data is made available in real-time after an FFT-based spectral analysis algorithm has been employed by the second signal analyzer. Shown are the resultant key frequency components: fundamental cardiac, harmonic cardiac, and satellite heart rate variability spectral lines. The number and magnitude of spectral lines are calculated by the second signal analyzer as the NUMBER of MAJOR PEAKS, shown as =30 in this illustrative embodiment.
Figure 11:
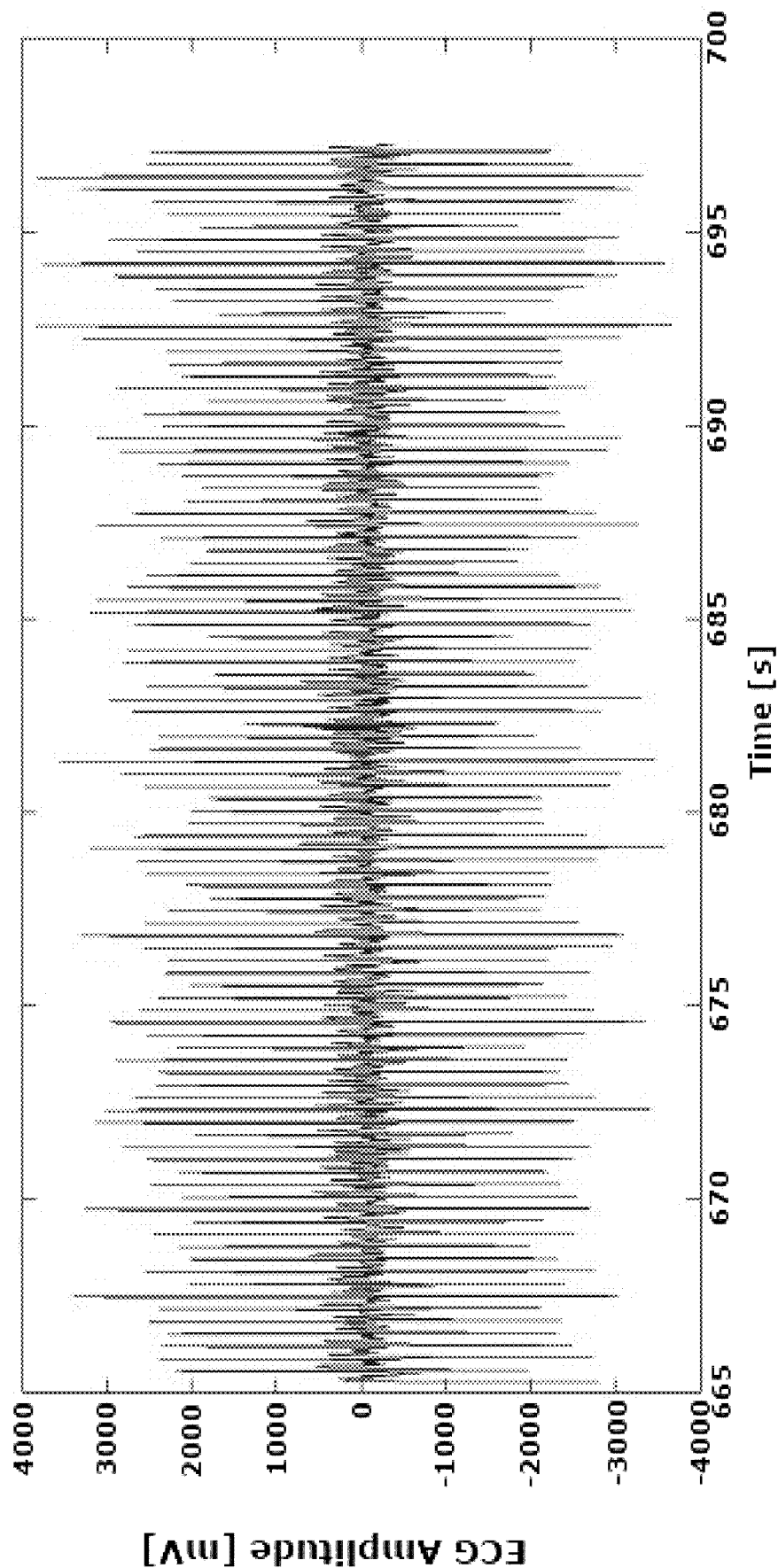
FIG. 11 is a time domain illustration of the electrocardiogram obtained from the chest belt apparatus utilized as a wearable lactate threshold device (LTD) in accordance with an exercise subject undergoing HEAVY exercise in an illustrative embodiment. Note the heart rate can easily be seen to continue to increase with the intensity of exercise activity
Figure 12:
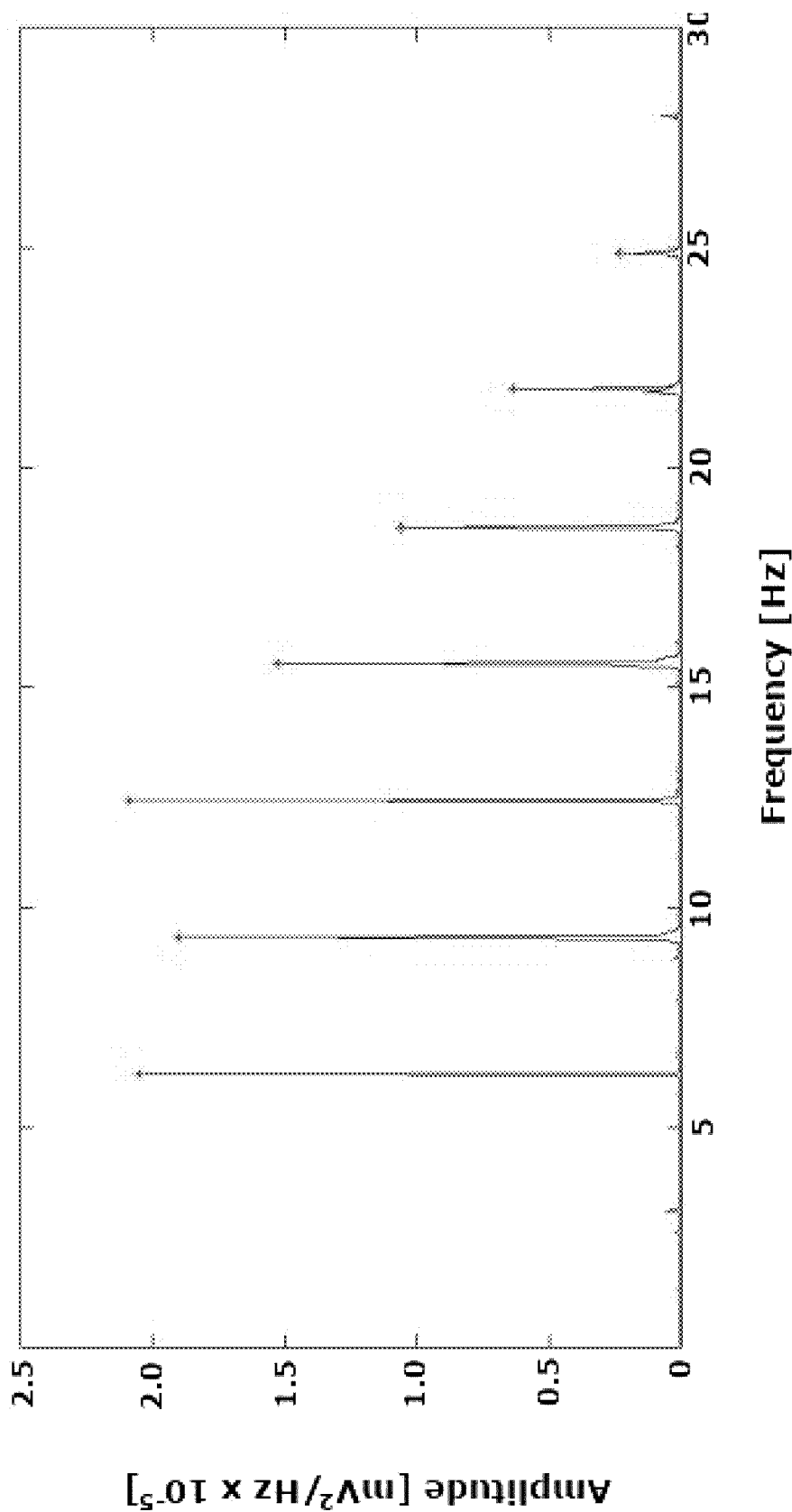
FIG. 12 is a frequency domain illustration of the electrocardiogram obtained from the chest belt apparatus utilized as a wearable lactate threshold device (LTD) in accordance with an exercise subject undergoing HEAVY exercise in an illustrative embodiment. Note the frequency domain data is made available in real-time after an FFT-based spectral analysis algorithm has been employed by the second signal analyzer. Shown are the resultant key frequency components: fundamental cardiac, harmonic cardiac, and satellite heart rate variability spectral lines. Note: it can easily be seen from this illustrative embodiment that the number of satellite heart rate variability spectral lines is markedly diminished and have reached the characteristic minima at lactate threshold. The number and magnitude of spectral lines are calculated by the second signal analyzer as the NUMBER of MAJOR PEAKS, shown as =7. When the NUMBER of MAJOR PEAKS is a minima, such as shown in this illustrative embodiment, the LTD detects and displays lactate threshold on the local and remote display, in real-time, in the field.

In an exercising subject example, FIGS. 7-12 are actual ECG signals in the time domain and frequency domain used to detect lactate threshold (LT) during MILD, MODERATE, and HEAVY exercise. FIG. 7, FIG. 9, and FIG. 11 are time domain ECG signals during MILD, MODERATE, and HEAVY exercise, respectively. FIG. 8, FIG. 10, and FIG. 12 are the same ECG signals transformed into the frequency domain during MILD, MODERATE, and HEAVY exercise, respectively. It can be easily observed that the number of major peaks (MP) between 0.4-30 Hz decreases from >100 to 30 to 7 during MILD, MODERATE, and HEAVY exercise, respectively. Since the number of major peaks=7 in this exercising subject, as calculated by the second signal analyzer, since the number of major peaks (MP) is a minima during HEAVY exercise, lactate threshold is detected, and the heart rate at lactate threshold=3.1 Hz or 187 bpm, as shown in FIG. 12. Heart Rate Zone 4 is thus built by the signal analyzer around this all important LT data point, and shown prominently on the real-time local or remote display as 182-197 bpm. Trainers and coaches may thus write prescriptive exercise regimens for the exercising subject to spend a prescribed amount of time in heart rate zone 4, that is, in order to improve competitive edge, and/or increase calorie burn. The remainder of exercise heart rate zones can easily be calculated from the heart rate at LT, as well as cycling/running power zones can also easily be calculated from the power (in Watts) at LT, as is well known to those skilled in the art. In this embodiment, heart rate or cycling/running power at LT occurs when number of major peaks <18. Note, in alternative embodiments, using a different electrocardiogram sample rate, a different window size, and/or a different FFT size, the number of major peaks (MP) needed to detect a minima may differ.

In summary, the LTD device has a first and second signal analyzer that uses an algorithm to calculate Lactate Threshold (LT) from an ECG as shown in the figures. In one embodiment, raw high fidelity electrocardiogram (ECG) data is sampled at 128 Hz and processed by a 4096 point Fast Fourier Transform (FFT) in a 32 sec rolling window into the frequency domain. Based on analysis of the ECG data in the frequency domain, the magnitude and frequency of the fundamental cardiac, harmonic cardiac, and satellite heart rate variability spectral lines are identified between 0.4-30 Hz. When the number of major peaks (MP) reaches a minima, or <18 in this embodiment, heart rate at Lactate Threshold is identified. With heart rate at Lactate Threshold identified, exercise heart rate zone 4 is calculated, and heart rate zones 1-5 are easily calculated thereafter, as is well known to those skilled in the art. In addition, cycling/running power zones can be calculated in a similar manner, that is, once power (in Watts) at Lactate Threshold is known, as well known to those skilled in the art.

This new and novel spectral-based algorithm in the frequency domain described herein for lactate threshold (LT) detection differs significantly from that typically used by Polar Electro Oy (U.S. Pat. No. 5,810,722). This time domain based algorithm to detect lactate threshold typically statistically analyzes R-R intervals via standard deviation or root mean square. Importantly, all of the known algorithms for lactate threshold analysis utilize time domain R-R interval data, and do not directly analyze or utilize ECG data, as is employed by the current invention. The time-domain LT algorithm published in Polar Electro Oy user guides (Kempele, Finland) for the S810 heart rate monitor utilize the R-R interval (that is, instantaneous heart rate data) time series, as is well known to those skilled in the art. The R-R interval time series is subsequently resampled at 4 Hz by interpolation of a third order spline function to obtain equidistant data, notably losing significant amounts of accuracy and precision in the process. After resampling this irregularly spaced time series, the R-R interval time series is prefiltered by a pass-band finite impulse response (FIR) filter corresponding to HF and LF frequency bands, in order to reduce noise. Another embodiment of this older time domain algorithm to detect lactate threshold is 'Kubios HRV—Heart Rate Variability Analysis Software' (www.kubios.com). This 'resampled R-R interval time series method' has similarly been recommended by the Task Force of the European Society of Cardiology and the North American Society of Pacing and Electrophysiology (1996). However, it is recognized by those skilled in the art this classic time-domain algorithm is imperfect and subject to error due to: (i) R-R interval time series being irregularly spaced data, requiring it to be resampled; and, (ii) being very prone to motion artifact during heavy exercise and heart rhythm arrhythmias and skipped beats causing significant interference to the LT calculation.

In one embodiment of the novel spectral-based algorithm described herein, a first analyzer in the two electrode 921 922 ECG signal acquisition conditioning circuit such as shown in FIG. 6 is improved on and developed using an oversampling method. Oversampling utilizes high speed analog to digital conversion (ADC) to markedly improve the signal-to-noise ratio of the 2-lead ECG signal detected from the exercise chest belt sub-system 100, as shown in FIG. 2. This oversampling method is especially important for noise reduction in the LTD device where only two electrodes are typically utilized, as a ground lead or a driven-right-leg electrode is typically not included for common mode noise rejection ratio (CMRR) noise reduction.

One embodiment of this novel LTD highly utilizes the concepts of the discrete Fourier transform (DFT) and fast Fourier transform (FFT) during heavy exercise. The DFT/FFT converts a finite list of equally spaced samples of a function into a list of coefficients of a finite combination of complex sinusoids, ordered by their frequencies. Fourier analysis can be implemented in computers by numerical algorithms, especially on microcontrollers 924 with dedicated hardware floating point units, or use of a second signal analyzer. The current LTD optimizes use of FFT-based spectral analysis by selecting sample rates and window sizes to minimize the problems of aliasing and leakage.

FFT-based spectral analysis is a particularly advantageous and primary method for digital signal processing for improving Heart Rate, HRV, and Electrocardiogram accuracies, by decreasing susceptibility to motion artifact, high skin impedance, and electronic artifact. The cardiac electrocardiogram signal of interest is a sinusoidal signal that is very capable of being transformed by the FFT into the frequency domain with resultant single spectral lines for the fundamental cardiac frequency. as well as the harmonic cardiac frequencies and satellite heart rate variability frequencies of interest.

All these spectral lines can easily be isolated via fourier analysis, even under HEAVY exercise conditions, in real-time, in the field. Finally, the LF-THM and HF-RSA frequencies of the autonomic nervous system can be easily isolated as well by using a long enough sample period and by selecting a window size to allow enough frequency bin resolution, as well as training the signal analyzer to look in particular for satellite frequencies due to heart rate variability, in particular around the cardiac harmonic spectral lines.

FFT-based spectral analysis is shown to be a practical solution. In one embodiment, the FFT is implemented on a unified signal analyzer, consisting of a microcontroller 924 with hardware floating point unit for full spectrum analysis, including frequency bins related to physiologic, exercise motion, and electrocardiogram waveforms, including LF-THM 0.03-0.15 Hz, HF-RSA 0.15 Hz-1.00 Hz, heart rate 0.6-3.7 Hz, exercise cadence 0.5-4.0 Hz, cardiac harmonic 0.4-30 Hz, and electrical/optical interference 50/60/120 Hz. In addition, FFT analysis improves accuracy, decreases susceptibility to motion artifact, and improves high skin impedance electrocardiogram signal analysis. In summary, FFT-based spectral analysis improves accuracy in the LTD for the calculated heart rate, HRV, lactate threshold, and exercise heart rate zone and cycling/running power zone variables.

The local or remote display sub-unit shown in FIG. 4 may self-guide subjects in improving athletic performance in the field, towards improving their fitness and competitive edge, towards maximizing their calorie burn, through visual feedback on the local or remote smartphone/smartwatch display. Feedback may also be given through audio, haptic, red/yellow/green dedicated LEDs, or other suitable methods.

FIG. 4 illustrates two remote display units (smart-watch and smart-phone) in accordance with an illustrative embodiment. Both units have an LCD display with a wireless telemetry module, and are capable of displaying digital values of heart rate, HRV, electrocardiogram, lactate threshold, and heart rate exercise zones as well as cycling/power exercise zones.

For example, the occurrence of lactate threshold may be represented by red-yellow-green stripes in the display units, or via discrete red-yellow-green LEDs. The observer may optionally see electrocardiogram waveforms both in the time and frequency domain, as well as number of major peaks (MP).

FIGS. 7-12 show example graphs for local or remote display units for exercise electrocardiogram time and frequency domain graphs, including instantaneous heart rate in the time domain graph, and number of major peaks (MP) in the frequency domain graph.

As shown in FIG. 4, display technology for wrist watches and other small devices and smartphones, well known to those skilled in the art, provide a very compact and useful battery-powered local or remote display during HEAVY exercise. A suitable smartwatch, wearable on the wrist, with suitable display, and Bluetooth 4.x transceiver, is the Mobvoi S2 Tic Watch (mobvoi.com, Beijing, China). A suitable smartphone with a suitable display and Bluetooth 4.x transceiver is the Palm Companion Android Phone (Palm, Inc., palm.com, San Francisco, Calif.). These local and remote displays may be utilized by the exercising subject, coach, or trainer, in order to follow along and adjust exercise physiology as needed during training or competition, or to maximize calorie burn and weight loss strategies.

For example, LT improves with exercise training, and, as a result, moves closer to the maximum metabolic and power output for any given individual (VO2max). Those who improve LT experience less physical deterioration in muscle cell performance and use less glycogen for ATP production at any level of performance. Thus, improvement in LT through prescribed training allows the athlete to perform at maximal levels for a longer period of time before running out of energy. In essence, an LT-trained athlete with high intensity interval training (HIIT) training under his belt may develop the physical fitness needed to defeat opponents that may have greater physical strength or determination.

The LT concept has famously led to the thoughtful design of exercise regimens that rapidly improve athletic performance, even at the Olympic and Professional Sports levels. Generally speaking, however, training intensity is not typically prescribed right at LT, but is either much higher or lower intensity. Periodic training at higher intensities than LT is the most valuable training, though is typically limited by coaches since an athlete can quickly over-train in the anaerobic training zone. In turn, assessing the work and power level at LT can be used to evaluate the results of an alternate high and low intensity exercise training program. That is, LT testing is the best marker to evaluate how long training hours are paying off for any athlete willing to wear and use this novel LTD invention.

The local or remote display enables coaches, trainers and athletes to measure both aerobic and anaerobic conditioning by better defining LT. Information about LT is necessary to optimize conditioning, whether the event is a 200 Meter Freestyle Swimming event or an Ironman Triathlon. With information on each aerobic and anaerobic energy system, a coach may plan, control and monitor the training of athletes with more precision and accuracy. LT data can individualize the intensity of each workout to prescribed exercise heart rate zones and cycling/running power zones, as are well known to those skilled in the art. Most importantly, this prescription cannot be made until LT is accurately and precisely known, as can be had in real-time with the current LTD invention. Classically, LT-based exercise zones have been previously prescribed not in real-time, but based on prior laboratory testing; or based upon age/weight/sex algorithms; or based upon relative perceived exertion. All of the classic LT-based exercise zones based upon these methods are prone to major inaccuracies. For example, LT may change day to day due to performance enhancing drugs like caffeine ingestion, outdoor temperature and humidity, wind speed, and whether or not a high speed fan is utilized during indoor LT laboratory testing. Also LT may change with time, or with changing fitness levels. It is evident and clear to those skilled in the art that all of these classic LT testing methods have serious shortcomings, shortcomings that have now been overcome in real-time fashion by this novel LTD invention. With the current LTD invention, training may be controlled in real-time, indoors or outdoors, wind or no wind, good or bad weather, day to day, with changing levels of overall fitness, to reach performance objectives in a stepwise process. With real-time LT-based training, there will likely be no over-training and minimal surprises come race day.

Because lactate is produced by the anaerobic system and used by the aerobic system, it has become a widely recognized and unique marker to measure each system. The amount of energy an athlete can produce per unit of time depends on the development of both aerobic and anaerobic systems, which is why each system is deliberately balanced through training regimens. Essentially, monitoring LT allows for training of the anaerobic system to a level that is appropriate for the athlete's aerobic capacity. This balance will depend upon the event for which the athlete is competing, and will also depend upon the crescendo of the training cycle. In essence, the closer the athlete gets to the "big" race-day event, the more the balance is fine-tuned for peak performance.

Over time, changes in LT reveal what physiological adaptations have taken place. It may tell the coach which forms of training are working or not working. Training time thus becomes much more efficient as the athlete performs only workouts that have benefit. LT becomes the training compass that steers each athlete in the right direction; LT based training is much more relevant than simple heart rate or power meter monitoring, which typically only reflect a general overall body response to stress. Traditional heart rate monitoring and power meter training cannot ever begin to reflect what is actually happening directly in the muscles or within the anaerobic system, except by knowing when and where LT occurs, now available with the current LTD invention in real-time in the field.

One way to effectively utilize the LTD is by targeting an effort level called maximal lactate steady state (MLSS) or Functional Threshold Power (FTP). MLSS and FTP is the maximal level of activity an athlete can continue for an extended period of time, e.g. about 20-60 minutes, without having to slow down. As long as the athlete maintains this effort level, the blood lactate level will remain constant, typically 4 mmol/L. At small effort levels above this point, lactate levels will rise, and the athlete will be forced to stop, sometimes even within a few minutes of the initial rise >4 mmol/L. Above MLSS and FTP there are no more steady states, the only option being an inevitable rapid progression to exhaustion. Training periodically at MLSS and FTP improves both sprint and endurance fitness levels dramatically, provides a competitive edge in formal competitions, and maximizes calorie burn for weight loss.

With prior art, time and power output at MLSS and FTP have been the best indicators of endurance performance. Importantly, prior to this current LTD invention, MLSS could only be verified through blood lactate testing, requiring a finger or ear skin needle prick. The athlete with the best MLSS and FTP will be faster and stronger in an endurance event. Increases in MLSS and FTP during training are almost always accompanied by improvements in race performance. For short events, such as swimming and rowing, MLSS and FTP are highly correlated with performance; in addition, anaerobic capacity is independently improved as well. The current LTD invention is designed to facilitate non-invasive MLSS and FTP training in real-time in the field, with no skin needle pricks or blood samples required.

It may be appreciated that throughout the specification discussions utilizing terms such as "processing," "computing," "calculating," "determining," or the like, these terms mainly refer to the action and/or processes of a computer or computing system, or similar electronic computing device; the signal analyzer through its software programmed algorithms manipulate and/or transform electrocardiogram data, digitizing physical analog electronic signals, into bitwise quantities within the computing system registers and/or memories, and then subsequently transformed again into other data, such as lactate threshold, heart rate, HRV, exercise heart rate power zones, cycling/running power zones, similarly represented as physical quantities within the computing system memories, registers or other such information storage, transmission or display devices.

In a similar manner, the term "processor" or "controller" may refer to any device or portion of a device that processes electronic data from registers and/or memory to transform that electronic data into other electronic data that may be stored in registers and/or memory. A "computing platform" may comprise one or more processors or controllers.

According to an exemplary embodiment, exemplary methods set forth herein may be performed by an exemplary computer processor(s) or controller(s) adapted to process program logic, which may be embodied on an exemplary computer accessible storage medium, which when such program logic is executed on the exemplary processor(s) or controller(s), may perform such exemplary steps via software and firmware programming, as set forth in the exemplary methods, algorithms, and digital signal processing.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Those of skill in the art will appreciate that the various illustrative logical blocks, modules, circuits, and algorithm steps described in connection with the embodiments disclosed herein may be implemented as electronic hardware, computer software, controller firmware, or combinations of both. To clearly illustrate this interchangeability of hardware and software and firmware, various illustrative components, blocks, modules, circuits, and steps have been described above generally in terms of their functionality. Whether such functionality is implemented as hardware or software or firmware depends upon the particular application and design constraints imposed on the overall system. Skilled artisans may implement the described functionality in varying ways for each particular application, but such implementation decisions should not be interpreted as causing a departure from the scope of the present disclosure.

Although the foregoing has included detailed descriptions of some embodiments by way of illustration and example, it will be readily apparent to those of ordinary skill in the art in light of the teachings of these embodiments that numerous changes and modifications may be made without departing from the spirit or scope of the appended claims.

In an illustrative embodiment, any of the operations described herein can be implemented at least in part as computer-readable instructions stored on a computer-readable medium or memory. Upon execution of the computer-readable instructions by a processor or controller, the computer-readable instructions can cause a computing device to perform the operations.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of this novel LTD invention be defined by the claims appended hereto and their equivalents.

Unless otherwise defined, each technical or scientific term used herein has the same meaning as commonly understood by one of ordinary skill in the art to which this disclosure belongs. In accordance with the claims that follow and the disclosure provided herein, the following terms are defined with the following meanings, unless explicitly stated otherwise.

The term "about" or "approximately," when used before a numerical designation or range (e.g., pressure or dimensions), indicates approximations which may vary by (+) or (−) 5%.

The term "substantially," when used in the context of substantially eliminating electrical interference, shall mean eliminating at least 95% of the interference present in a detected signal.

As used in the specification and claims, the singular form "a", "an", and "the" include both singular and plural references unless the context clearly dictates otherwise. For example, the term "an electrocardiogram" may include, and is contemplated to include, a plurality of electrocardiograms. At times, the claims and disclosure may include terms such as "a plurality," "one or more," or "at least one"; however, the absence of such terms is not intended to mean, and should not be interpreted to mean, that a plurality is not conceived for a particular embodiment.

As used herein, the term "comprising" or "comprises" is intended to mean that the devices, systems, and methods include the recited elements, and may additionally include any other elements. "Consisting essentially of" shall mean that the devices, systems, and methods include the recited elements and exclude other elements of essential significance to the combination for the stated purpose. Thus, a device or method consisting essentially of the elements as defined herein would not exclude other materials or steps that do not materially affect the basic and novel characteristic(s) of the claimed LTD invention. "Consisting of" shall mean that the devices, systems, and methods include the recited elements and exclude anything more than a trivial or inconsequential element or step. Embodiments defined by each of these transitional terms are within the scope of this disclosure.

What is claimed is:

1. A portable system for a user to detect a lactate threshold comprising:
    said portable system comprising an electrocardiogram chest belt, said electrocardiogram chest belt comprised of,
        at least two electrodes electrically coupled to a first signal analyzer, wherein said first signal analyzer gathers, conditions, and digitizes a raw electrocardiogram high fidelity signal from the electrodes, thereby generating a digital time domain electrocardiogram signal;
    a second signal analyzer, said second signal analyzer having one or more processors, said one or more processors of said second signal analyzer adapted to receive said digital time domain electrocardiogram signal, wherein said second signal analyzer performs Fast Fourier Transform spectral analysis, wherein said digital time domain electrocardiogram signal is transformed by said second signal analyzer into a frequency domain electrocardiogram signal;
    wherein said second signal analyzer analyzes said frequency domain signal, determining a plurality of parameters comprising heart rate, heart rate variability, and characteristics of major peaks of said frequency domain signal, said major peaks comprising:
        fundamental cardiac spectral lines,
        harmonic cardiac spectral lines, and
        satellite heart rate variability spectral lines;
    said characteristics comprising number, frequency, and magnitude of said major peaks;
    wherein said second signal analyzer detects occurrence of the lactate threshold by detection of a minima in said number of major peaks;
    a first telemetry unit, said first telemetry unit electrically coupled to said first signal analyzer, a second telemetry unit electrically coupled to said one or more processors of said second signal analyzer, wherein said first telemetry unit adapted to wirelessly transmit said digital time domain electrocardiogram signal to said one or more processors of said second signal analyzer via said second telemetry unit, and further wherein said one or more processors of said second signal analyzer adapted for local or remote display of the electrocardiogram and resultant processed data, said resultant processed data comprising: said lactate threshold, and optionally including,
    said major peaks, and/or
    said characteristics.

2. The portable system of claim 1, wherein said portable system is configured for high intensity interval training, comprising:

wherein said second signal analyzer provides a determination whether said user has entered into an anaerobic training zone by analyzing said number of major peaks;

wherein said second signal analyzer monitors the user's time spent in the anaerobic training zone;

wherein said second signal analyzer provides instructions for said user to decrease training activity to enter an aerobic training zone after a first designated time is spent training in the anaerobic training zone;

wherein a determination is made whether the user has entered into the aerobic training zone by analyzing said number of major peaks;

wherein said second signal analyzer monitors the user's time spent in the aerobic training zone;

wherein said second signal analyzer provides instructions for the user to increase training activity to enter the anaerobic training zone after a second designated time is spent training in the aerobic training zone;

wherein said second signal analyzer designates, tracks, and displays time spent in the anaerobic training zone and time spent in the aerobic training zone, which may optionally be configured by the user;

wherein the first designated time spent in the anaerobic training zone and the second designated time spent in the aerobic training zone are configured to automatically adjust according to a predetermined training program.

3. The portable system of claim 1, further comprising, wherein said second signal analyzer provides a lactate threshold evaluation, wherein values for exercise heart rate zones and cycling/running power zones are computed and displayed, the values being based upon a detected heart rate at the lactate threshold, and a functional threshold power at the lactate threshold;

wherein the lactate threshold evaluation assesses whether a maximal lactate steady state has been reached, wherein the maximal lactate steady state and the functional threshold power have been reached when lactate levels approach, maintain, but do not cross the lactate threshold; and wherein the lactate threshold evaluation provides instructions to guide the user in obtaining and maintaining maximal lactate steady state and functional threshold power for a prolonged period of time in a range of 20-60 minutes.

* * * * *